US007938791B2

(12) United States Patent
Shishido

(10) Patent No.: US 7,938,791 B2

(45) Date of Patent: May 10, 2011

(54) GUIDE MECHANISM AND WALKING ASSIST DEVICE

(75) Inventor: Makoto Shishido, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 0 days.

(21) Appl. No.: 12/557,110

(22) Filed: Sep. 10, 2009

(65) Prior Publication Data

US 2010/0114330 A1 May 6, 2010

(30) Foreign Application Priority Data

Nov. 6, 2008 (JP) ................................ 2008-285829

(51) Int. Cl.
*A61F 5/00* (2006.01)
*A61H 1/00* (2006.01)

(52) U.S. Cl. .................. 602/23; 602/18; 602/16; 601/5

(58) Field of Classification Search .................... 602/19, 602/16, 23, 26, 27; 607/49, 48; 601/5, 33, 601/34, 35; 623/27; 482/66, 124

See application file for complete search history.

(56) References Cited

U.S. PATENT DOCUMENTS 7,549,969 B2 * 6/2009 van den Bogert ............... 602/16

FOREIGN PATENT DOCUMENTS

JP 2007-020909 2/2007

* cited by examiner

*Primary Examiner* — Michael Brown
*Assistant Examiner* — Ophelia Hawthorne
(74) *Attorney, Agent, or Firm* — Rankin, Hill & Clark LLP

(57) ABSTRACT

A guide mechanism 100 is equipped with a guiding body 31 including a guiding trajectory, and a movable body 32 guided so as to move along the guiding trajectory. The guide mechanism 100 is further equipped with an elastic body 102 of a coil shape with one end thereof being connected to the movable body 32 and extends along the guiding body 31 from the one end thereof, and a first supporting body 106 and a second supporting body 108 which supports the elastic body 102 along the guiding body 31. An electric wiring W for connecting electric equipments together is inserted into the elastic body 102.

18 Claims, 5 Drawing Sheets

GUIDE MECHANISM AND WALKING ASSIST DEVICE

BACKGROUND OF THE INVENTION

1. Field of the Invention

The present invention relates to a guide mechanism which guides a movable body along a guiding trajectory of an arc shape, and a walking assist device utilizing the guide mechanism.

2. Description of the Related Art

Conventionally, as this type of a walking assist device, there is known one which comprises a seat member where a user sits astride, and leg links which supports the seat member from therebelow, wherein the walking assist device assists walking of the user by relieving the load acting on the legs of the user, by receiving at least a part of the weight of the user by the leg link via the seat member (refer to Japanese Patent Laid-open No. 2007-020909).

The seat member and the leg links are connected via a curved guide mechanism comprised of a guiding body including a guiding trajectory which is connected to the seat member and having an arc shape which is longitudinal in an anteroposterior direction with a center of curvature thereof above the seat member, and a movable body which is connected to the upper end of the leg link and which is movably coupled to the guiding trajectory via a plurality of rotating bodies.

However, according to the conventional technique mentioned above, it is necessary to transmit signals from various sensors provided to the leg link to the control device provided on the seat member side, in order to relieve the load acting on the legs, of the user and to assist walking. Thereafter, it is necessary for the control device to control a driving source provided to the leg link on the basis of the signals from the various sensors.

Therefore, it is necessary to connect the control device provided on the seat member side and the various sensors and the driving source provided to the leg link with an electric wiring.

However, there is a problem that the electric wiring may be tangled with the guiding body or the movable body that are moving bodies of the curved guide mechanism.

SUMMARY OF THE INVENTION

In view of such circumstances, an object of the present invention is to provide a guide mechanism which is capable of preventing the moving body from becoming tangled with a connecting member, when connecting equipments moving relatively with the connecting member, and to provide a walking assist device utilizing the guide mechanism.

In order to achieve the above object, the present invention provides a guide mechanism, comprising: a guiding body including a guiding trajectory; a movable body which is guided so as to move along the guiding trajectory; an elastic body with one end thereof fixed to the movable body, and which extends from the one end along the guiding body; and a supporting body which supports the elastic body along the guiding body; wherein the elastic body is inserted with a connecting member which connects equipments together.

According to the guide mechanism with the above configuration, the connecting member connecting the equipments is inserted into the elastic body supported along the guide member. Therefore, it is possible to prevent the moving body from becoming tangled with the connecting member, when connecting the equipments moving relatively with the connecting member.

In the guide mechanism of the present invention, it is preferable that the supporting body is comprised of a pair of a first supporting body and a second supporting body provided across a slit formed at a center in a groove width direction on an outer peripheral wall of the guiding body.

According to the guide mechanism with the above configuration, the connecting member connecting the equipments moving relatively is guided reliably by the first supporting body and the second supporting body.

In the guide mechanism of the present invention, it is preferable that the supporting body is formed so as to make an opening of a cross-sectional surface of the first supporting body and the second supporting body face each other, and the elastic body extends from the location connected to the movable body towards the front of the second supporting body, is bent at a predetermined location of the guiding body and extends to the rear of the first supporting body.

According to the guide mechanism with the above configuration, the connecting member connecting the equipments moving relatively is guided reliably by the first supporting body and the second supporting body that are formed so as to face each other at the opening in the cross-section.

In the guide mechanism of the present invention, it is preferable that the elastic body is formed into a coil shape.

According to the guide mechanism with the above configuration, the connecting member connecting the equipments moving relatively is guided reliably by the coil-shaped elastic body.

In order to solve the above problem, the present invention provides a walking assist device, equipped with a seat member where a user sits astride, and leg links supporting the seat member from therebelow; in which the seat member and the leg links are connected via a curved guide mechanism, the curved guide mechanism being comprised of a guiding body which is connected to the seat member and is provided with a guiding trajectory of an arc shape which is longitudinal in the anteroposterior direction and which has a center of curvature above the seat member, and a movable body connected to the upper end of the leg link and which is coupled to the guiding trajectory so as to be able to move freely via a plurality of rotating bodies; the walking assist device is equipped with an elastic body of a coil shape, one end thereof is connected to the movable body and extends along the guiding body from the one end thereof; and a supporting body which supports the elastic body along the guiding body; wherein the elastic body is inserted with a wiring member used for electrical connection.

According to the walking assist device of the present invention, the electric wiring connecting the control device provided on the seat member side and the various sensors and the driving source provided to the leg link is inserted into the elastic body which is supported along the guiding body. Therefore, it is possible to prevent the electric wiring and the guiding body or the movable body as the moving body of the curved guide mechanism from becoming tangled.

DETAILED DESCRIPTION OF THE PREFERRED EMBODIMENTS

Figure 1:
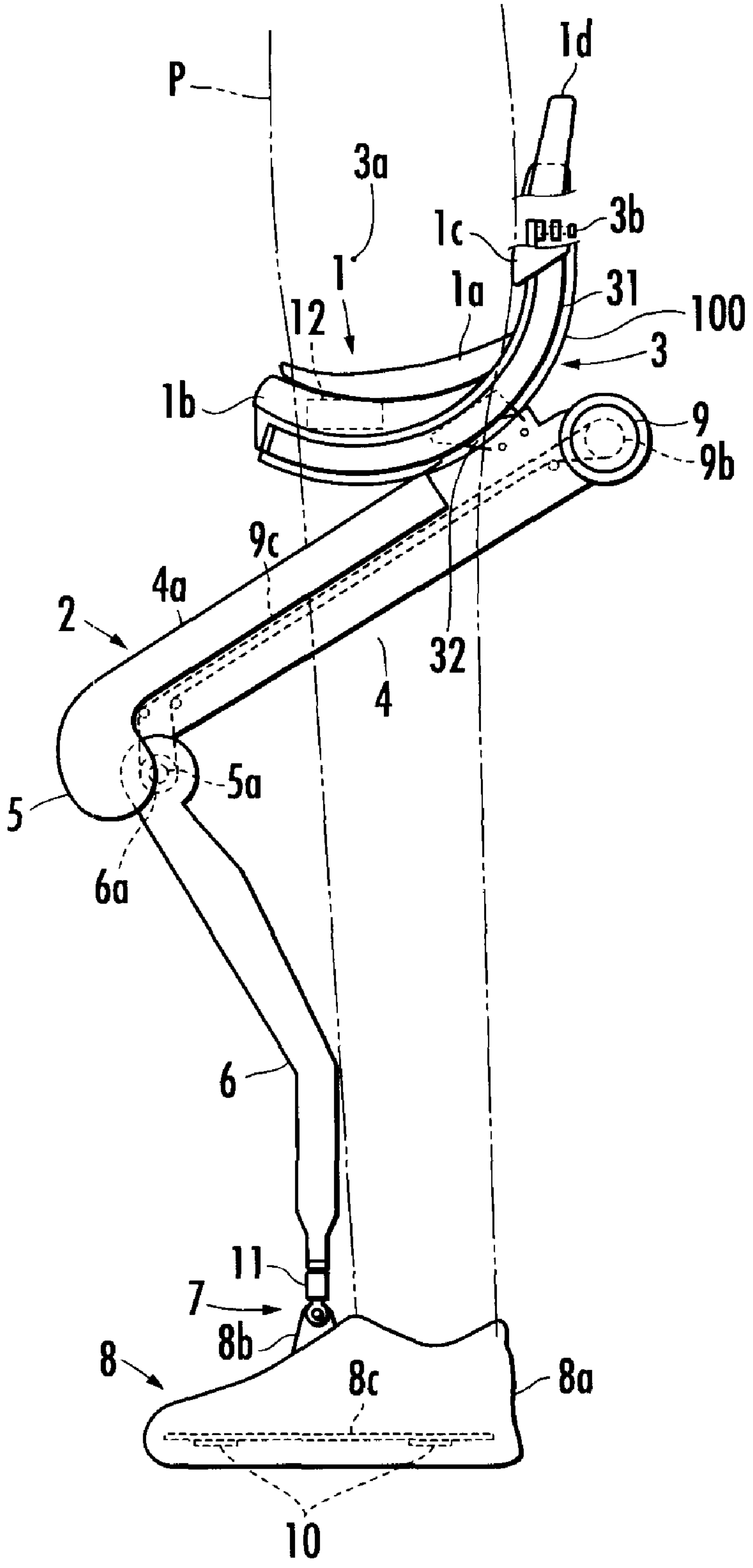
FIG. 1 is a front view of an example of a walking assist device of the present invention.
Figure 2:
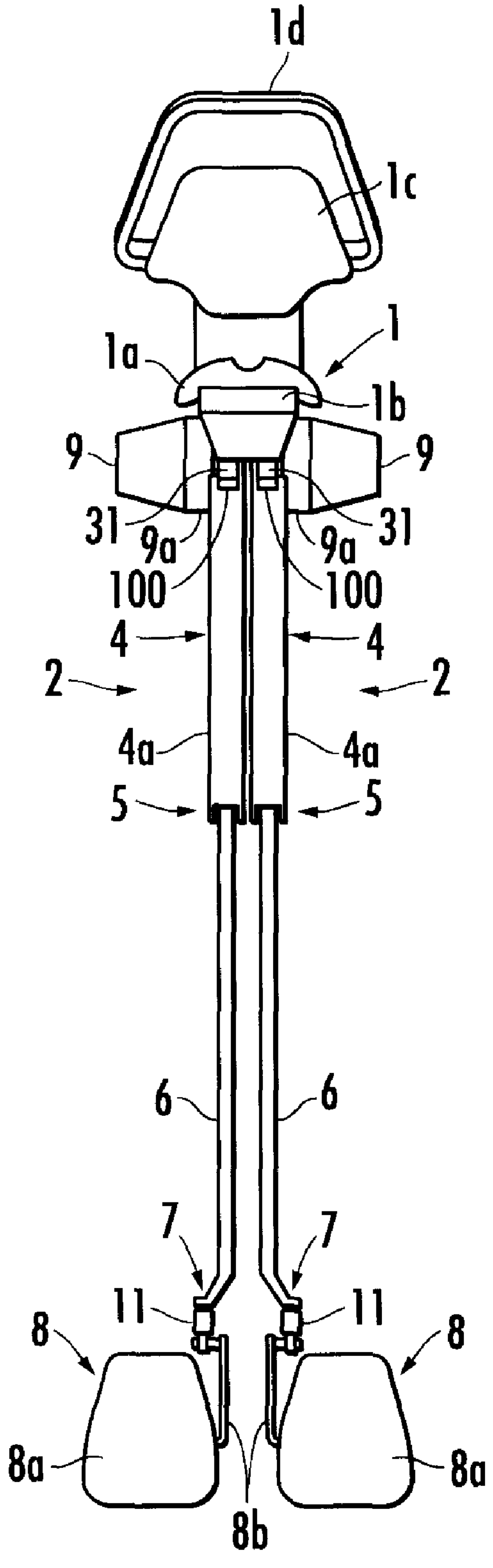
FIG. 2 is a side view of an example of the walking assist device of the present invention.

A walking assist device shown in each of FIG. 1 and FIG. 2 includes a seat member 1 where a user P sits astride, and a pair of right and left leg links 2, 2 supporting the seat member 1 from therebelow.

Each leg link 2 is configured from a link capable of bending and stretching freely. The link is configured from a thigh link 4 connected to the seat member 1 through a curved guide mechanism 3 explained hereinafter so as to be able to swing freely in the anteroposterior direction, and a crus link 6 connected to the lower end of the thigh link 4 via a rotary type knee joint 5. Further, a foot attachment portion 8 fitted to each of the right and left foot of the user P is connected to the lower end of the crus link 6 via an ankle joint 7.

Each leg link 2 is equipped with a driving source 9 for the knee joint 5. Thereby, according to the rotation of the knee joint 5 driven by the driving source 9, each leg link 2 is actuated in a stretching direction, so as to generate an assist force to support at least a part of a body weight of the user P (hereinafter, referred to as a body weight relieving assist force). The body weight relieving assist force generated in each leg link 2 is transmitted to the body trunk of the user E via the seat member 1 to relieve the load acted on the leg of the user P.

The driving source 9 is configured from an electric motor with a reduction gear 9*a* fixed to the outer surface at the upper end of the thigh link 4. An output member of the reduction gear 9*a*, that is, a driving pulley 9*b*, and a driven pulley 6*a* which is fixed to the crus link 6, are connected via a wrapping transmission member 9*c*, such as a wire, a chain, a belt or the like. The driven pulley 6*a* is arranged so as to be concentric to a joint axis 5*a* of the knee joint 5.

According to such structure, a driving force output from the driving source 9 via the reduction gear 9*a* is transmitted to the crus link 6 via the wrapping transmission member 9*c* so that the crus link 6 swings around the joint axis 5*a* with respect to the thigh link 4 to bend or stretch the leg link 2. A cover 4*a* which covers the wrapping transmission member 9*c* is fixed to the thigh link 4.

The seat member 1 is configured from a seat portion 1*a*, a support frame 1*b*, and a hip cushion 1*c*. The seat portion 1*a* is of a saddle shape to be seated by the user P. The support frame 1*b* is disposed below the seat portion 1*a* to form an uprising portion at a rear end thereof. The hip cushion 1*c* is disposed at the uprising portion. A holding portion 1*d* of an arch shape is provided to the hip cushion 1*c* for being held by the user P.

Each foot attachment portion 8 is comprised of a shoe 8*a* and a connection member 8*b* which is fixed to the shoe 8*a* and extends upward. The crus link 6 of each leg link 2 is connected to the connection member 8*b* via the ankle joint 7 of a 3-axis structure.

A pair of longitudinally disposed pressure sensors 10, 10, which detect loads acted on the metatarsophalangeal joint (MP joint) and the heel of each foot of the user P, respectively, are attached to the undersurface of an insole 8*c* provided in the shoe 8*a* (refer to FIG. 1). Further, a two-axis force sensor 11 is built into the ankle joint 7. The detected signals from the pressure sensor 10 and the force sensor 11 are input to a controller 12 stored in the supporting frame 1*b* of the seating member 1.

The controller 12 drives the knee joint 5 of the leg link 2 by controlling the driving source 9 on the basis of the signals from the pressure sensor 10 and the force sensor 11, and executes the walking assist control which generates the body weight relieving assist force mentioned above.

The assist force, when viewed in the lateral direction, is acted on a connection line (hereinafter, referred to as a reference line) joining a swing fulcrum 3*a* of the leg link 2 with respect to the seat member 1 in the anteroposterior direction and a swing fulcrum of the leg link 2 at the ankle joint 7 in the anteroposterior direction.

In the walking assist control, the actual assist force acted or the reference line (more accurately, a resultant force between the assist force and a force generated by the self weight of the seat member 1 and each leg link 2) is calculated based on the detected value of a force in a biaxial direction detected by the force sensor 11.

Thereafter, on the basis of the detection pressure by the pressure sensor 10 in each foot attachment portion 8, a ratio of the load acted on each foot with respect to the total load acted on both feet of the user P is calculated.

Then, a desired control value of the assist force which should be generated for each leg link 2 is calculated by multiplying a predetermined set value of the assist force by the ratio of the load acted on each foot. Subsequently, the driving source 9 is controlled so that the actual assist force calculated on the basis of the detected value of the force sensor 11 becomes the desired control value.

Next, explanation will be given on a guide mechanism 100 to be applied to the walking assist device of the present invention.

The guide mechanism 100 is of a structure of a harness connecting the controller 12 provided on the seat member 1 side, and the driving source 9, the pressure sensor 10 and the force sensor 11 that are provided on the leg link 2 with an electric wiring (connecting member) W. The guide mechanism 100 is configured from a curved guide mechanism 3, an elastic body 102 and a supporting body 104.

The curved guide mechanism 3 includes a guiding trajectory connected to the seat member 1. The guiding trajectory is of an arc shape which is longitudinal in the anteroposterior direction and has a center of curvature 3*a* above the seat member 1. The curved guide mechanism 3 is configured from a guiding body 31 which is connected to the uprising portion at the rear end of the supporting frame 1*b* of the seat member 1 via a spindle 3*b* in the anteroposterior direction so as to be able to swing freely in the lateral direction, and a movable body 32 connected to the upper end of the leg link 2 and which is coupled to the guiding trajectory so as to be able to move freely via a plurality of rotating bodies. A guiding groove 33 of an arc shape which is longitudinal in the anteroposterior direction and which becomes the guiding trajectory is formed to the guiding body 31. The center of curvature 3*a* of the arc shape of the guiding groove 33 is positioned above the upper surface of the seat la of the seat member 1.

Figure 3:
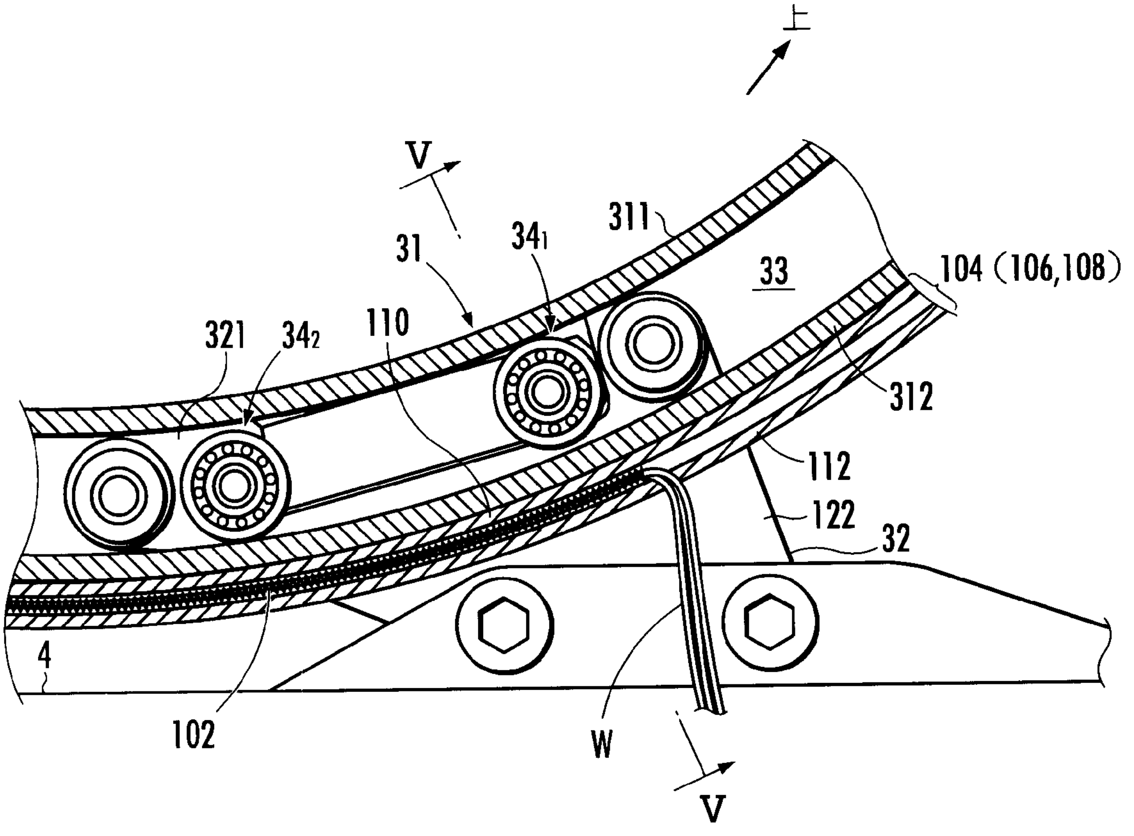
FIG. 3 is a partial cross-sectional view of a curved guide mechanism of the walking assist device.
Figure 4:
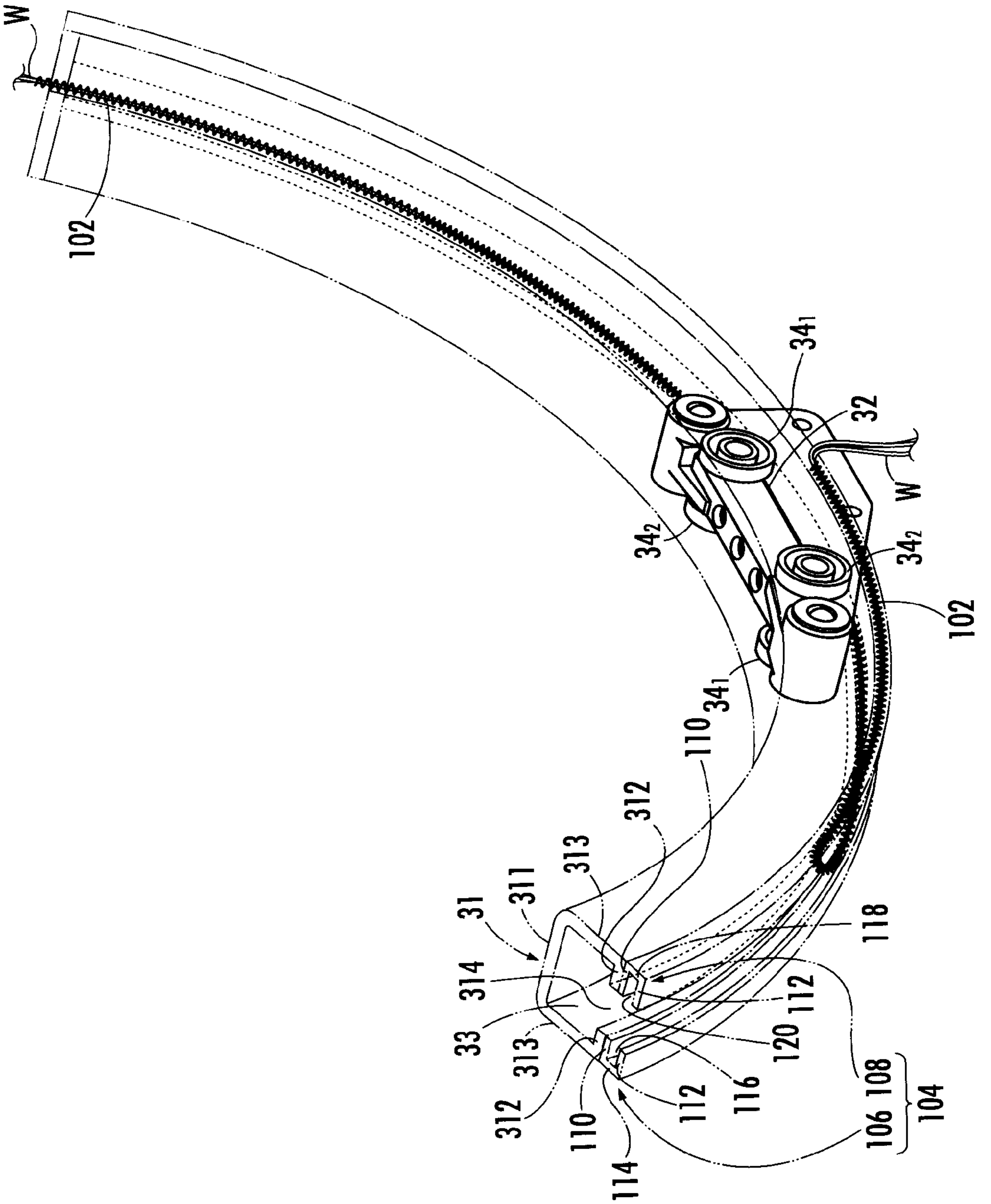
FIG. 4 is a perspective view of the curved guide mechanism of the walking assist device.
Figure 5:
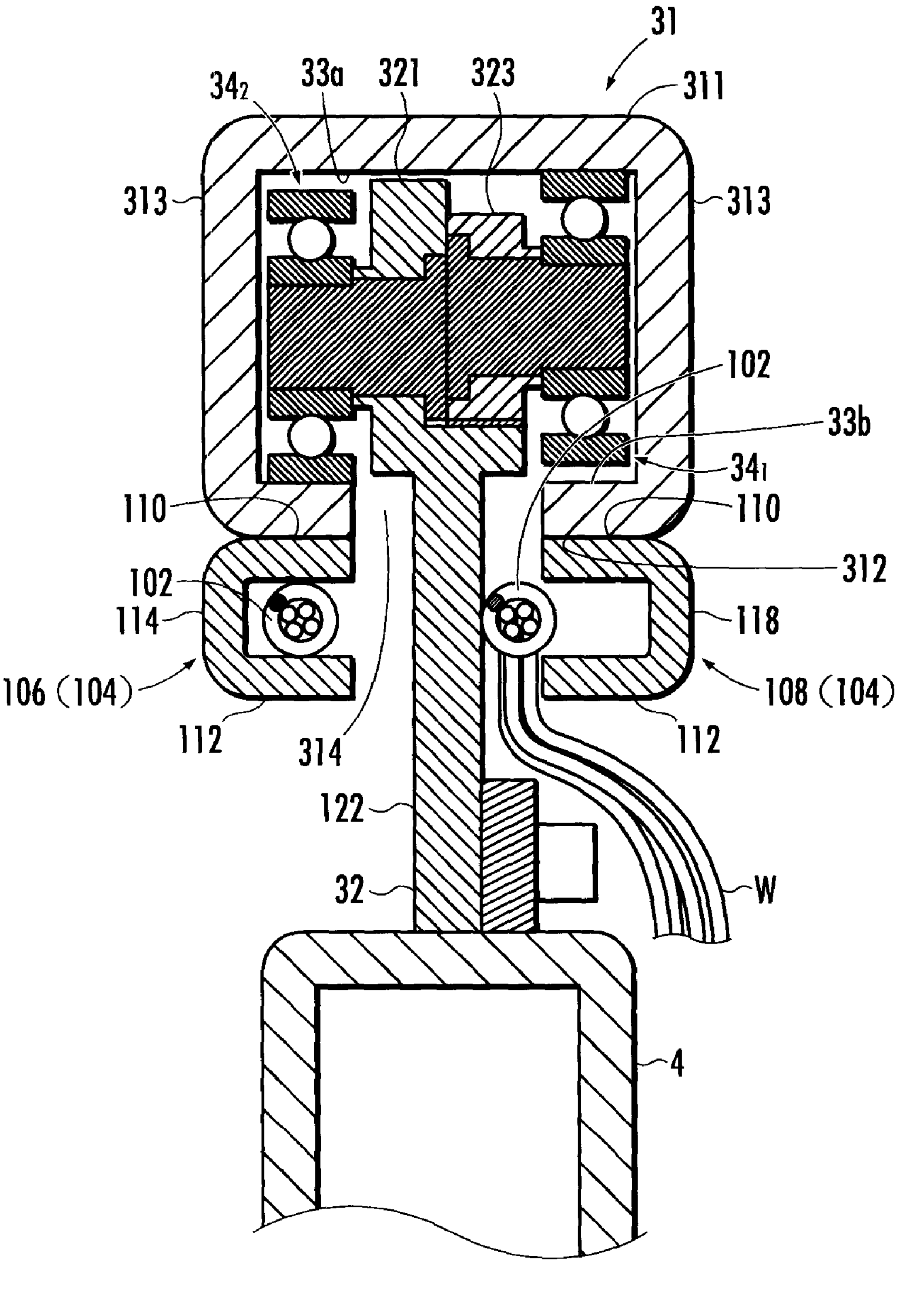
FIG. 5 is a cross-sectional view taken along a line V-V in FIG. 3.

Next, with reference to FIG. 3 through FIG. 5, explanation will be given in more detail on the configuration of the guiding body 31, the movable body 32, the elastic body 102 and the supporting body 104, respectively.

The guiding body 31 is comprised of a cross-sectionally C-shaped molded material including an inner circumferential wall 311, an outer circumferential wall 312, a pair of vertical walls 313, 313, and a slit 314. A guiding groove 33 is formed by partitioning the interior space of the molded material. The inner circumferential wall 311 configures an inner circumferential groove wall surface 33*a* which is closer to the center of curvature 3*a* of the guiding groove 33. The outer circumferential wall 312 configures an outer circumferential groove wall 33_b_ which is farther from the center of curvature 3_a_ of the guiding groove 33. The pair of vertical walls 313, 313 connects the inner circumferential wall 311 and the outer circumferential wall 312 at both sides of a groove width direction (lateral direction) which is orthogonal to both the longitudinal direction (anteroposterior direction) of the guiding groove 33 and a radius of curvature direction (vertical direction) of the arc shape. The slit 314 is formed at a center in the groove width direction of the outer circumferential wall 312. In FIG. 4, the leg link 2 is omitted therefrom.

The movable body 32 includes an insert 321 to be inserted to the guiding groove 33 through the slit 314 of the guiding body 31. On one side of the groove width direction of the insert 321 and on the other side thereof, there is each provided a row of rotating bodies. The row of rotating bodies is comprised of one inner rotating body $34_1$ and one outer rotating body $34_2$ arranged apart from one another in the longitudinal direction of the guiding groove 33. That is, to the movable body 32, there are provided two rows of the row of rotating bodies in which the row of rotating bodies is arranged apart from each other in the groove width direction.

The elastic body 102 is a coil-like elastic body, with one end thereof connected to the movable body 32 and which extends along the guiding body 31 from the one end. To the elastic body 102, there is inserted the electric wiring W which electrically connects the controller 12 provided on the seat member 1 side, and the driving source 9, the pressure sensor 10, and the force sensor 11 provided to the leg link 2. One example of the elastic body 102 is a coil spring.

The supporting body 104 is configured so as to support the elastic body 102 along the guiding body 31. The supporting body 104 is provided under the guiding body 31 and along the guiding body 31. The supporting body 104 is configured from a pair of a first supporting body 106 and a second supporting body 108. The pair of the first supporting body 106 and the second supporting body 108 are arranged across the slit 314 formed et the center in the groove width direction of the outer circumferential wall 312 of the guiding body 31.

The first supporting body 106 is formed into a cross-sectionally C-shape from a supporting inner circumferential wall 110, a supporting outer circumferential wall 112, and a supporting vertical wall 114. The supporting inner circumferential wall 110 is provided on the outer circumferential wall 312 of the guiding body 31, so as to extend in the longitudinal direction of the guiding body 31. The supporting outer circumferential wall 112 is provided below the supporting inner circumferential wall 110 with a predetermined distance therebetween. The supporting vertical wall 114 connects the supporting inner circumferential wall 110 and the supporting outer circumferential wall 112 at the inner sides thereof. A first support groove 116 is formed by partitioning to the first supporting body 106.

The second supporting body 108 is formed into a cross-sectionally C-shape from the supporting inner circumferential wall 110, the supporting outer circumferential wall 112, and a supporting vertical wall 118. The supporting inner circumferential wall 110 is provided on the outer circumferential wall 312 of the guiding body 31, so as to extend in the longitudinal direction of the guiding body 31. The supporting outer circumferential wall 112 is provided below the supporting inner circumferential wall 110 with a predetermined distance therebetween. The support vertical wall 118 connects the supporting inner circumferential wall 110 and the supporting outer circumferential wall 112 at the outer sides thereof. A second support groove 120 is formed by partitioning to the second supporting body 108.

Therefore, the first supporting body 106 and the second supporting body 108 both has a cross-section of a C-shape, and faces each other at the opening thereof.

The elastic body 102 has one end 124 thereof fixed to a protrusion 122 where the movable body 32 protrudes downwardly from the guiding body 31.

When the movable body 32 is positioned at the center of the guiding body 31, the elastic body 102 extends from the portion connected to the protrusion 122 of the movable body 32 to the front of the second support groove 120 of the second supporting body 108, is bent at a predetermined portion of the guiding body 31, and further extends to the rear of the first support groove 116 of the first supporting body 106.

According to the guide mechanism of the present embodiment and the walking assist device equipped with the guide mechanism, the electric wiring W connecting the controller 12 provided on the seat member 1 side, and the driving source 9, the pressure sensor 10 and the force sensor 11 provided to the leg link 2, is inserted into the elastic body 102 supported along the guiding body 31. Therefore, it is possible to prevent the electric wiring W from being tangled with the guiding body or the movable body 32 that are the movable body of the curved guide mechanism 3.

In the present embodiment, the connecting member connecting the equipments is the electric wiring W. However, the connecting member may be an air pipework, a hydraulic pipework and the like.

What is claimed is:

1. A guide mechanism, comprising:

a guiding body including a guiding trajectory;

a movable body which is guided so as to move along the guiding trajectory;

an elastic body with one end thereof fixed to the movable body, and which extends from the one end along the guiding body; and a supporting body which supports the elastic body along the guiding body;

wherein the elastic body is inserted with a connecting member which connects equipments together.

2. The guide mechanism according to claim 1,wherein the supporting body is comprised of a pair of a first supporting body and a second supporting body provided across a slit formed at a center in a groove width direction on an outer peripheral wall of the guiding body.

3. The guide mechanism according to claim 2, wherein the supporting body is formed so as to make an opening of a cross-sectional surface of the first supporting body and the second supporting body face each other, and the elastic body extends from the location connected to the movable body towards the front of the second supporting body, is bent at a predetermined location of the guiding body and extends to the rear of the first supporting body.

4. The guide mechanism according to claim 1, wherein the guiding body and guiding trajectory have an elongated arcuate shape.

5. The guide mechanism according to claim 4, wherein the movable body is movable from a first position along the guiding trajectory to a second position along the guiding trajectory.

6. The guide mechanism according to claim 1, wherein the supporting body is secured to the guiding body and extends along a length of the guiding trajectory.

7. The guide mechanism according to claim 6, wherein the supporting body defines at least one substantially C-shaped member in which the elastic body is received.

8. The guide mechanism according to claim 1, wherein the connecting member is inserted into the elastic body.

9. The guide mechanism according to claim 8, wherein the elastic body encloses a portion of the connecting member disposed within the guiding body.

10. The guide mechanism according to claim 1, wherein the elastic body is formed into a coil shape.

11. The guide mechanism according to claim 1, wherein the one end of the elastic body is fixed directly to the movable body.

12. The guide mechanism according to claim 1, wherein the connecting member is an electric wiring and the elastic body is configured to have the electric wiring inserted therewith.

13. The guide mechanism according to claim 1, wherein the connecting member is an air pipework and the elastic body is configured to have the air pipework inserted therewith.

14. The guide mechanism according to claim 1, wherein the connecting member is a hydraulic pipework and the elastic body is configured to have the hydraulic pipework inserted therewith.

15. The guide mechanism according to claim 1, wherein the guiding body has an elongated shape such that the guiding trajectory defines a path along which the movable body is movable.

16. The guide mechanism according to claim 1, wherein the elastic body is substantially contained within the supporting body.

17. The guide mechanism according to claim 1, wherein the movable body comprises a plurality of rotating bodies operably engaging the guiding body.

18. A walking assist device, equipped with a seat member where a user sits astride, and leg links supporting the seat member from therebelow; in which the seat member and the leg links are connected via a curved guide mechanism, the curved guide mechanism being comprised of a guiding body which is connected to the seat member and is provided with a guiding trajectory of an arc shape which is longitudinal in the anteroposterior direction and which has a center of curvature above the seat member, and a movable body connected to the upper end of the leg link and which is coupled to the guiding trajectory so as to be able to move freely via a plurality of rotating bodies;

the walking assist device is equipped with an elastic body of a coil shape, with one end thereof is connected to the movable body and which extends along the guiding body from the one end thereof; and a supporting body which supports the elastic body along the guiding body;

wherein the elastic body is inserted with a wiring member used for electrical connection.

* * * * *